(12) United States Patent
Dvir et al.

(10) Patent No.: US 9,114,009 B2
(45) Date of Patent: Aug. 25, 2015

(54) NANOWIRED THREE DIMENSIONAL TISSUE SCAFFOLDS

(75) Inventors: Tal Dvir, Rishon le Zion (IL); Daniel S. Kohane, Newton, MA (US); Robert S. Langer, Newton, MA (US); Brian Timko, Cambridge, MA (US)

(73) Assignees: Children's Medical Center Corporation, Boston, MA (US); Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 13/997,939

(22) PCT Filed: Dec. 28, 2011

(86) PCT No.: PCT/US2011/067554
§ 371 (c)(1),
(2), (4) Date: Jun. 25, 2013

(87) PCT Pub. No.: WO2012/094208
PCT Pub. Date: Jul. 12, 2012

(65) Prior Publication Data
US 2013/0289687 A1 Oct. 31, 2013

Related U.S. Application Data

(60) Provisional application No. 61/430,043, filed on Jan. 5, 2011.

(51) Int. Cl.
*A61F 2/24* (2006.01)
*A61L 27/44* (2006.01)
*A61N 1/05* (2006.01)
*B82Y 5/00* (2011.01)

(52) U.S. Cl.
CPC .............. *A61F 2/2418* (2013.01); *A61L 27/44* (2013.01); *A61N 1/0597* (2013.01); *B82Y 5/00* (2013.01); *Y10S 977/762* (2013.01)

(58) Field of Classification Search
CPC ......... A61F 2/2418; A61I 7/44; A61N 1/0597
USPC ............ 607/129; 424/93.7; 75/370; 454/93.7
See application file for complete search history.

(56) References Cited

U.S. PATENT DOCUMENTS

| 2003/0153965 | A1  | 8/2003  | Supronowicz |
| 2006/0006463 | A1* | 1/2006  | Islam et al. ............... 257/347 |
| 2007/0142916 | A1  | 6/2007  | Olson |
| 2007/0289409 | A1* | 12/2007 | Xia et al. ............... 75/370 |

(Continued)

OTHER PUBLICATIONS

Cellot, et al., "Carbon nanotubes might improve neuronal performance by favouring electrical shortcuts", Nature Nanotech.,4:126-33 (2009).

(Continued)

*Primary Examiner* — Christopher D Koharski
*Assistant Examiner* — Michael Carey
(74) *Attorney, Agent, or Firm* — Pabst Patent Group LLP

(57) ABSTRACT

Electrically conductive nanowires incorporated within scaffolds enhance tissue growth, bridge the electrically resistant pore walls and markedly improve electrical communication between adjacent cardiac cell bundles. Integration of conducting nanowires within 3D scaffolds should improve the therapeutic value of cardiac patches. Examples demonstrate efficacy of gold nanowires in alginate matrices seeded with cardiomyocytes.

20 Claims, 5 Drawing Sheets

(56) References Cited

U.S. PATENT DOCUMENTS

2009/0098184 A1* 4/2009 Govil et al. .................. 424/423
2009/0117087 A1* 5/2009 Carroll et al. ................ 424/93.7
2012/0065703 A1* 3/2012 Paukshto et al. ................ 607/50

OTHER PUBLICATIONS

Chen, et al., "An elastomeric patch derived from poly(glycerol sebacate) for delivery of embryonic stem cells to the heart", Biomaterials, 31(14):3885-93 (2010).

Cohen-Karni, et al., "Flexible electrical recording from cells using nanowire transistor arrays", PNAS, 106:7309-13 (2009).

Dvir, et al., "Prevascularization of cardiac patch on the omentum improves its therapeutic outcome", PNAS, 106:14990-5 (2009).

Dvir, et al., "Activation of the ERK1/2 cascade via pulsatile interstitial fluid flow promotes cardiac tissue assembly". Tissue Eng., 13:21825-93 (2007).

Engelmayr, et al., "Accordion-like honeycombs for tissue engineering of cardiac anisotropy", Nature Mat., 7:1003-10 (2008).

Giraud, et al., "Long-term evaluation of myoblast seeded patches implanted on infarcted rat hearts", Artif Organs, 34(6):E184-92 (2010).

Ito, et al., "Use of an expanded polytetrafluoroethylene patch as an artificial leaflet in mitral valve plasty: an early experience", Ann Thorac Surg.,89(5):1620-4 (2010).

Miyagi et al., "Surgical ventricular restoration with a cell- and cytokine-seeded biodegradable scaffold", Biomaterials, (2010).

Radisic, et al., "Medium perfusion enables engineering of compact and contractile cardiac tissue", Am. J. Physiol. Heart Circ. Physiol., 286:H507-16 (2004).

Radisic, et al., "Functional assembly of engineered myocardium by electrical stimulation of cardiac myocytes cultured on scaffolds", PNAS, 101:18129-34 (2004).

Sachlos, et al., "Collagen scaffolds reinforced with biomimetic composite nano-sized carbonate-substituted hydroxyapatite crystals and shaped by rapid prototyping to contain internal microchannels". Tissue Eng., 12:2479-87 (2006).

Shachar, et al., "The effect of immobilized RGD peptide in alginate scaffolds on cardiac tissue engineering", Acta Biometer., 7(1):152-62 (2011).

Singelyn, et al., Injectable materials for the treatment of myocardial infarction and heart failure: the promise of decellularized matrices J Cardiovasc Transl Res., 3(5):478-86 (2010).

Souza, et al., "Three-dimensional tissue culture based on magnetic cell levitation", Nat Nanotechnol., 5:291-6 (2010).

Timko, et al., "Electrical recording from hearts with flexible nanowire device arrays", Nano Letters, 9:914-8 (2009).

Wu, et al., "A biomimetic hierarchical scaffold: natural growth of nanotitanates on three-dimensional microporous Ti-based metals", Nano Letter, 8:3803-8 (2008).

Zimmermann, et al., "Tissue engineering of a differentiated cardiac muscle construct", Circ.Res., 90:223-30 (2002).

* cited by examiner

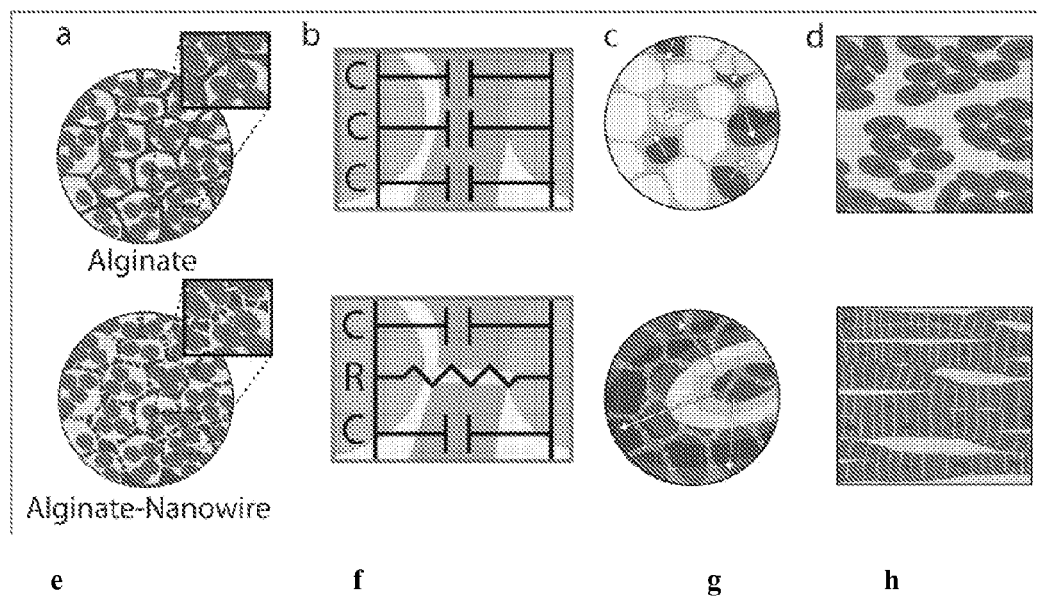
FIGURES 1A-H
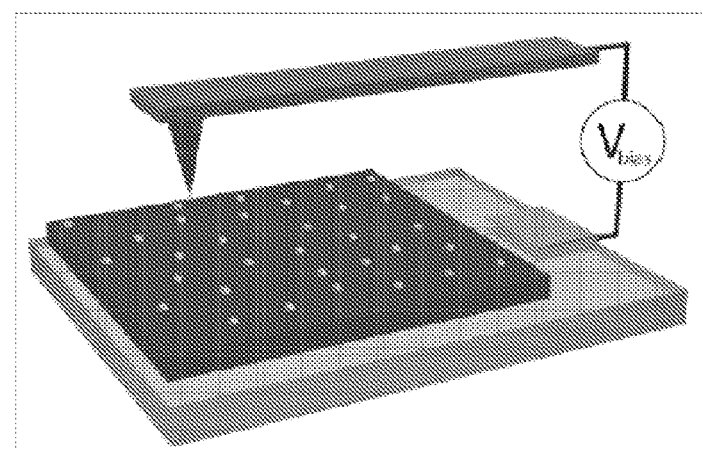
FIGURE 2A

NANOWIRED THREE DIMENSIONAL TISSUE SCAFFOLDS

STATEMENT REGARDING FEDERALLY SPONSORED RESEARCH OR DEVELOPMENT

This invention was made with government support under Grant GM073626 awarded by the National Institutes of Health. The U.S. Government has certain rights in the invention.

CROSS REFERENCE TO RELATED APPLICATIONS

This application is a 371 application of the published International Application No. PCT/2012/067554, entitled "Nanowired Three Dimensional Tissue Scaffolds", by Tal Dvir, Daniel S. Kohane, Robert S. Langer, and Brian Timko, filed Dec. 28, 2011, which claims the benefit of and priority to U.S. Ser. No. 61/430,043, filed Jan. 5, 2011, all of which are herein incorporated in their entirety by reference.

FIELD OF THE INVENTION

This application is generally in the field of tissue engineering, and in particular is drawn to electrically conductive cardiac patches for repair of tissue damaged by myocardial infarction.

BACKGROUND OF THE INVENTION

The urgent need to improve the viability, ultrastructural morphology and functionality of engineered cardiac tissue has been addressed by growing cell constructs in advanced bioreactors providing high mass transfer or exposing the tissues to electrical (Radisic, M., et al. *Pro. Na. Acad. Sci. USA* 101, 18129-18134 (2004)) and mechanical cues (Zimmermann, W. H., et al. *Circ. Res.* 90, 223-230 (2002); Dvir, et al. *Tissue Eng.* 13, 2185-2193 (2007)). Scaffold structural and mechanical properties can be improved by microfabrication processes that provide controllable stiffness and anisotropy (Engelmayr, G. C., et al. *Nature Mat.* 7, 1003-1010 (2008)).

Engineered cardiac patches to replace scar tissue after myocardial infarction can be produced by seeding cardiac cells within porous three dimensional ("3D") biomaterials, which provide mechanical support while cells organize into a functioning tissue. However, success can be jeopardized by a lack of electrical conductivity within the construct. Electrical signal propagation between cardiomyocytes in separate pores is impeded by biomaterial resistance, limiting the patch's potential to contract strongly as a unit.

It is therefore an object of the present invention to provide tissue engineering scaffolds which can provide electrical stimulation to cardiomyocytes seeded into or onto the scaffolds.

SUMMARY OF THE INVENTION

Electrically conductive nanowires incorporated within scaffolds enhance tissue growth, bridge the electrically resistant pore walls and markedly improve electrical communication between adjacent cardiac cell bundles. Examples demonstrate efficacy of gold nanowires in alginate matrices seeded with cardiomyocytes.

Methods of manufacture and use thereof are also described.

BRIEF DESCRIPTION OF THE DRAWINGS

FIGS. 1A-H are schematics of the function of 3D nanowired cardiac tissue. FIGS. 1A and 1E show isolated cardiomyocytes cultured in either pristine alginate (1A) or alginate-nanowire ("Alg-NW") composites (1E). FIGS. 1B and 1F show that nanowire elements form conductive bridges across the nonconducting alginate. The equivalent circuit (expanded view) can be represented by capacitors (alginate) and resistors (NWs) connected in parallel. FIGS. 1C and 1G show that whereas cardiomyocytes in pristine alginate scaffolds (1C) typically form only small clusters that beat asynchronously and with random polarization, Alg-NW scaffolds (1G) exhibit synchronization across scaffold walls, throughout the entire scaffold. FIGS. 1D and 1H show that cardiomyocytes cultured in alginate scaffolds form (1D) small beating clusters, but that synchronously-beating cardiomyocytes can form (1H) striated cardiac-like tissue.

FIGS. 2A-2E are schematics and graphs showing the increase in electrical conductivity of alginate achieved with incorporation of NWs. FIG. 2A is a prospective view of a device used to measure spatial conductivity using C-AFM. The ITO slide served a backside contact, while the conductive AFM probe was used to simultaneously measure surface topography and conductance through the film. FIG. 2B is topographic mapping revealing NWs coming out of the composite alginate thin film (5×5 µm). FIG. 2C is a graph of the spatial conductivity within the Alg-NW film as measured by C-AFM. Current spikes were measured at the location of the NWs. FIG. 2D is a graph of the current measured at the NWs (red) increased with bias voltage over the range −1 to 1V, while negligible current passed through NW-free regions of the alginate film (blue) over that same range. FIG. 2E is a graph of the overall impedance of the scaffold biomaterial before and after modification with NWs. Thin layers of Alg-NW or pure alginate films were pressed between two ITO glass slides. These slides served as electrodes and were used to apply an AC bias with frequency swept between 1 MHz and 10 Hz. At frequencies near DC, the impedance of the composite membrane was much lower than that of the pure film.

FIG. 4A is a graph of dynamic viscosity (Pa*s) versus frequency. FIG. 4B is a graph of elastic shear modulus (G'(Pa)) versus frequency. Pink Asterick—1 mg/ml ANW; Green Square—0.5 mg/ml ANW; Blue triangle—0.25 mg/ml ANW; Red diamond—0.1 mg/ml ANW; and Purple x—alginate. N=3 for each testing.

DETAILED DESCRIPTION OF THE INVENTION

Figures 2B, 2C:
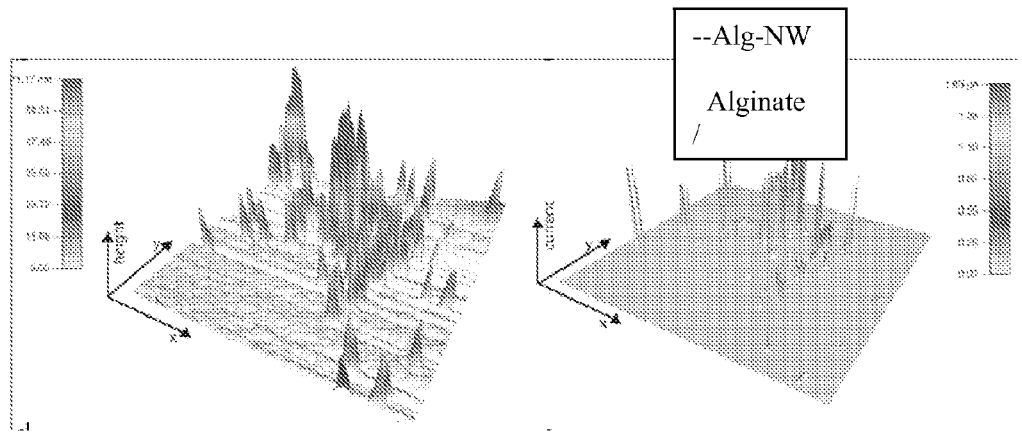
Figure 2D:
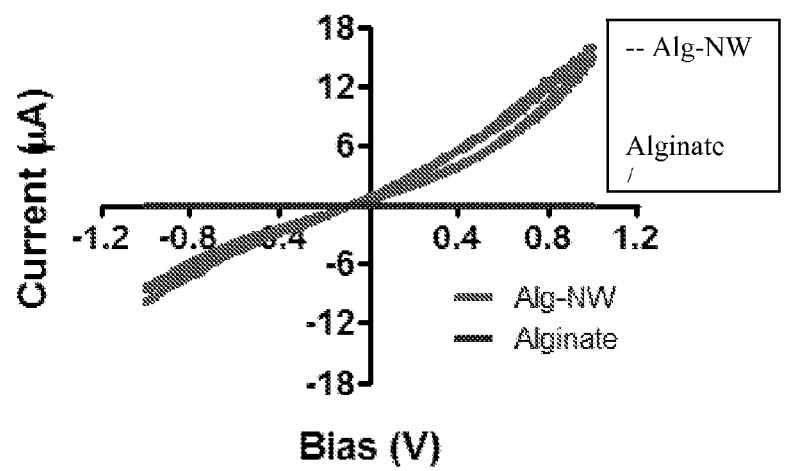

Nanoscale features that interact with the cells during cultivation have been incorporated into matrices in order to mimic the hierarchical nanostructure of the extracellular matrix and foster tissue morphogenesis and functionality. Moreover, a variety of nanostructures have the potential to compensate for matrix limitations such as weak mechanical properties, the absence of adhesive properties and the inability of cells to self-assemble in 3D, see Sachlos, et al. *Tissue Eng* 12, 2479-2487 (2006); Souza, G. R., et al. Three-dimensional tissue culture based on magnetic cell levitation. *Nat Nanotechnol* 5, 291-296 (2010); and Wu, S. L., et al. *Nano Letters* 8, 3803-3808 (2008).

The walls of the porous matrices currently used for cardiac tissue engineering limit cell-cell interaction and delay electrical signal propagation. This shortcoming is addressed by incorporating conductive nanomaterials within a construct. Inorganic nanostructures can be made to interact with cardiomyocytes, e.g. to create electronic interfaces (Timko, B. P., et al. *Nano Letters* 9, 914-918 (2009); Cohen-Karni, et al. *Proc. Nat. Acad. Sci. USA* 106, 7309-7313 (2009)), and can enhance cellular conductivity, for example by creating electrical shortcuts within neurons (Cellot, G., et al. *Nature Nanotech.* 4, 126-133 (2009)).

I. Nanocomposite

A 3D nanocomposite of gold nanowires (NWs) embedded within a macroporous scaffold such as the alginate-NW composite shown in FIGS. 1A-H has been developed.

A. Matrix Materials

Alginate was selected as a model biomaterial as it shares common characteristics, such as defined porous structure and lack of electrical conductivity, with other frequently used scaffolds. Other materials can be used including natural materials such as extracellular matrix, collagen, hyaluronic acid, chitosan, and other protein or polysaccharide material, and synthetic materials such as biodegradable polymers like the polyhydroxy acids polylactic acid, polyglycolic acid and copolymers thereof, polyhydroxyalkanoates such as poly4-hydroxybutyrate and copolymers thereof, all of which are FDA approved for use in humans. Poly(4-hydroxybutyrate) is available from Tepha Inc of MA and has been used in studies of heart valve leaflets made from woven meshes. Non-biodegradable materials such as polypropylene, polyethylene, polyurethanes, and other polyesters can also be used.

For example, Miyagi, et al., Biomaterials 2010 Oct. 28, reported on the use of a biodegradable collagen patch for delivery of vascular epithelial growth factor ("VEGF") for myocardial repair. Alginate scaffolds are described by Shachar, et al., in Acta Biomater. 2011 January; 7(1):152-62. Decellularized matrices are described by Singelyn, et al. in J Cardiovasc Transl Res. 2010 October; 3(5):478-86. Polymeric woven or non-woven matrices can be utilized. For example, non-biodegradable polyurethane matrices having seeded therein myoblasts is reported by Giraud, et al., in Artif Organs. 2010 June; 34(6):E184-92. Ito, et al., reported on the use of a polytetrafluorethylene (PTEF) patch in Ann Thorac Surg. 2010 May; 89(5):1620-4. Fibrinogen matrices or TachoSil, a sponge impregnated with human fibrinogen and thrombin, can be used. Chen, et al., describes an elastomeric patch derived from poly(glycerol sebacate) for delivery of cardiomyocytes differentiated from embryonic stem cells to the heart in Biomaterials. 2010 May; 31(14):3885.

B. Nanowire Construction

The design criteria for the synthesis of the NWs take two main factors into consideration. First, the wire length scale needed to ensure wall penetration and interaction with cells on both sides should be longer than the average thickness of the matrix pore wall, typically about 500 nm. Second, cell adhesion and spreading are impaired by interactions with structures with diameters larger than 50 nm, resulting in reduced cellular activity and increased apoptosis. To address these constraints, gold NWs have been synthesized by anisotropic gold seed elongation that exhibited an average length of 2-3 μm and average diameters of 30 nm. The NWs (1 mg/mL) assembled within the pore walls of the scaffold into star-shaped structures with a total length scale of 5 μm. The assembled wires were distributed homogenously within the matrix with a distance of approximately 5 μm from each other.

The nanowires preferably are formed of a highly conductive material, most preferably gold, platinum, or nickel, although other materials such as copper and stainless surgical steel may also be utilized. Gold is preferred due to its relatively inertness in the body.

In another embodiment, the nanowire is a molecular nanowire. Molecular nanowires, sometimes referred to as molecular wires, are molecular-scale objects which conduct electrical current. The diameters of molecular nanowires are typically on the order of less than three nanometers. However, their bulk lengths may be macroscopic, extending to centimeters or more.

The molecular nanowire can be organic or inorganic. Examples of organic and inorganic molecular nanowires include, but are not limited to, DNA and DNA-like molecules; inorganic polymeric materials such as $Li_2Mo_6Se_6$ and $Mo_6S_{9-x}I_x$; single-molecule extended metal atom chains (EMACs) which contain strings of late transition metal atoms directly bonded to each other; charge transfer complexes, such as bis-tetrathiafulvalene substituted macrocycle and tetrafluorotetracyanoquinodimethane; and pthalocyanine molecular wires.

C. Cells

In the preferred embodiment, the cells are seeded into and onto the scaffold. Most preferably these are autologous cells obtained by biopsy and enzymatic digestion of the tissue to dissociate the cells. In the preferred embodiment for repair of damaged cardiac tissue, cells are cardiomyocytes. Cells may be differentiated, multi or pluripotent (i.e., stem cells), or a combination thereof. Cells may be cultured initially in vitro to expand the number of cells available. Cells may also be seeded into the implant and then cultured in vitro prior to implantation.

D. Other Active Agents

The NW fabrication method allows further functionalization or incorporation of therapeutic, diagnostic, or prophylactic agents such as growth factors or other proteins or small molecules to be delivered in a controlled manner, further optimizing the engineered tissue.

II. Methods of Manufacture

In the exemplified method, the structures are formed as described in Example 1.

III. Methods of Use

In the preferred embodiment, the cells are obtained by biopsy from the individual in need of treatment. Cultured cells can also be used, as well as fresh cells from an allograft.

These are seeded onto the patch for immediate implantation or cultured in vitro, followed by implantation.

In another preferred embodiment, the patch is placed at the site in need of treatment and cells migrate into the patch, where they are stimulated to form a cohesive functional unit. This can be achieved using a pace maker, for example.

The present invention will be further understood by reference to the following non-limiting examples.

Example 1

Analysis of Cardiac Cell Organization within a 3D Alginate Scaffold with or without Gold Nanowires Materials and Methods A nanocomposite scaffold of alginate and NWs (Alg-NW) was created by mixing NWs with sodium alginate, followed by cross-linking with calcium gluconate and lyophilization. The scaffolds were 5 mm in diameter and 2 mm height.

Preparation of Gold NWs

First, citrate-capped Au seeds were prepared. A 20 mL aqueous solution of $HAuCl_4$ (0.25 mM) and sodium citrate (0.25 mM) was prepared. Under vigorous stirring, 0.6 mL ice-cold aqueous $NaBH_4$ solution (0.1 M) was added all at once. The solution immediately turned deep red, consistent with the formation of colloidal gold. A typical product contained spherical gold particles about 4 nm in diameter at an estimated density of ca. $7.6 \times 10^{13}$ particles/ml. The suspension was allowed to stand at room temperature (about 25° C., RT) for several hours before subsequent use to ensure complete degradation of the $NaBH_4$. The gold colloid was stable at 4° C. for at least several months.

Wires were grown by anisotropic elongation of the seeds. To achieve high aspect ratio nanowires, the reaction was carried out in three stages, in 25-ml Erlenmeyer flasks (Flasks A and B) and a 250-ml round-bottom flask (Flask C). First, Growth Solution was prepared. 7.54 g CTAB (0.1 M) was dissolved in 200 ml DI water at 37° C. After complete dissolution of the CTAB, $HAuCl_4$ was added (0.25 mM) followed by the addition of ascorbic acid (0.5 mM). The solution changed from deep to pale yellow, consistent with the reduction of Au(III) to Au(I). Finally, $HNO_3$ was added. The Growth Solution was then divided between Flask A (9 mL), Flask B (18 mL), and Flask C (173 mL). Nanowire growth was initiated by adding 1 mL Seed Solution to Flask A under vigorous stirring. After 15 s, 1 mL solution was transferred from Flask A to Flask B, with vigorous stirring. After 30 s, 5 mL solution was transferred from Flask B to Flask C, with vigorous stirring. The solution in Flask C was maintained at 37° C. with stirring, and turned deep purple over the course of 2 hrs. The solution contained a mixture of morphologies and was subsequently purified. The solution was collected in 50-mL centrifuge tubes, which were then situated in a 37° C. oven undisturbed for about 1 week. During this time, a brown pellet, which contained >90% wires, formed at the bottom of each tube. The supernatant was discarded, and the pellets were resuspended in DI water. A typical synthesis yielded ca. 60 mg product after purification.

Preparation of Alg-NW and Alginate Scaffolds

The 3D Alg-NW or alginate scaffolds were prepared from pharmaceutical grade alginate, Protanal LF 5/60 (FMC Biopolymers, Drammen, Norway), which has a high guluronic acid (G) content (65%). The method for Alg-NW scaffold preparation is a five-step process, consisting of: (i) preparation of sodium alginate stock solutions at concentrations of 1% (w/v); (ii) mixing NW solution (1 mg/mL) with the alginate solution followed by rapid mixing (iii); crosslinking of the alginate/NW solution by adding the bivalent cross-linker (e.g., calcium gluconate); (iv) freezing the cross-linked alginate in a homogeneous, cold (−20° C.) environment; and (v) lyophilization to produce a sponge like scaffold (5 mm×2 mm, d×h). The scaffolds were sterilized with UV light before use and were 90% porous with pore sizes ranging from 50 to 100 μm in diameter. Alginate scaffolds were prepared in the same manner without step (ii).

Cardiac Patch Construction, Cultivation and Analysis

Cardiac cells were isolated from the left ventricles of SD neonatal (0-1 day old) rat hearts and seeded onto either Alg-NW or alginate scaffolds (5×2 mm, d×h, $0.7 \times 10^8$ cells/$cm^3$). The cell-seeded constructs were cultured for 3 days in normal conditions (humidified incubator 5% $CO_2$, 37° C., no electrical field). At that point, constructs (both with NWs and pure alginate) were subjected to electrical stimulation (rectangular, 2 ms, 5 V/cm, 1 Hz) as described by Radisic, *Amer. J. Physiol.-Heart Circul. Physiol.* 286, H507-H516 (2004). Briefly, the constructs were cultivated in a glass chamber fitted with two ¼-inch-diameter carbon rods (Ladd Research Industries, Burlington, Vt.) placed 1 cm apart and connected to a cardiac stimulator (S88 Grass dual output square pulse stimulator, Astro-med Inc. RI) with platinum wires (Ladd Research Industries). At the end of the cultivation period, the patches were analyzed for viability using the XTT assay as described by Dvir, T., et al. *Proc Nat. Acad. Sci. USA* 106, 14990-14995 (2009) (n≥4 for each data point, collected from 2 separate experiments), or stained.

For histology, the cellular constructs were dehydrated in graduated alcohol steps (70-100%), paraffin-embedded, cut into 5-mm-thick sections, and mounted on slides. The sections were stained with hematoxylin and eosin (H&E). For immunofluorescence, the cellular constructs were fixed and permeabilized in cold methanol, blocked for 1 h at room temperature in Dulbecco's modified Eagle's medium (DMEM)-based buffer containing 5% FBS. After three buffer washes, the samples were incubated for 1 h with anti-troponin I or connexin 43 antibodies. After incubation, the samples were washed and incubated for 1 h with secondary antibodies. For nuclear detection, the cells were incubated for 3 min with Hoechst 33258 and washed. Imaging was performed with a DeltaVision RT deconvolution microscope using the 20× or 40× objective (Applied Precision Inc. Northwest Issaquah, Wash.).

Results

H&E figures of thin sections of the engineered tissues on day 8 revealed non-continuous tissue separated by pore walls in the pristine alginate scaffold, while in the NW scaffold the engineered tissue is thicker with elongated and aligned morphology. NWs are seen within the pore walls of a relatively empty region of a scaffold). In a higher cellular portion of a scaffold, wires within the wall were in close proximity to cell aggregates. Immunostaining of the cell seeded scaffolds on day 8 revealed pervasive troponin I expression within the Alg-NW scaffold, while reduced staining was observed within the aggregates formed in the un-modified scaffolds. Connexin 43 gap junction protein was found between cardiomyocytes in the NW-containing scaffolds.

The effect of bridging the pore walls of the scaffolds with NWs on the organization of cardiac cells was studied after culture for 3 days under static conditions followed by 5 days of cultivation under electrical field stimulation to improve cell alignment. Typically, cardiac cells seeded in pristine alginate scaffolds do not bind to the matrix, and organize into tight, rounded aggregates (<200 μm) within the pores. Hematoxylin and eosin (H&E) staining of histological sections at day 8 revealed that thick, intact and better-aligned tissue had formed within the Alg-NW scaffolds compared to the small aggregates within the alginate scaffold. NWs were seen in pore walls at the end of the cultivation period (day 8), suggesting that the wires remained integrated inside the scaffold walls throughout the cultivation period. H&E-stained thin sections of cells seeded at lower concentrations revealed that wires in the alginate walls were in close proximity to bundles of cells in adjacent pores.

The phenotype of the engineered tissue was evaluated by immunostaining for the expression of troponin I, which has a role in muscle calcium binding and contraction, and for the gap junction protein connexin 43, a molecule responsible for electrical and mechanical coupling. On day 3, cardiac cells within the Alg-NW scaffold expressed higher levels of both proteins. Immunostaining on day 8 revealed strong troponin I fluorescence and cells located throughout the Alg-NW scaffolds, unlike findings in the pristine scaffolds. Moreover, in the Alg-NW cultures connexin 43 detected between adjacent cardiomyocytes suggested maturation of the cardiac tissue. This was not seen in the unmodified matrix. These findings show that the NW imparted phenotypic traits consistent with enhanced contractile properties and electrical and mechanical coupling.

Example 2

Analysis of Calcium Transient Propagation within a 3D Alginate Scaffold with or without Gold Nanowires Seeded with Cardiac Cells Materials and Methods Calcium transient propagation within the engineered tissues was assessed at specified points by monitoring calcium dye fluorescence. Calcium transient was assessed at specified points by monitoring calcium dye fluorescence.

Neonatal rat ventricular myocytes were incubated with 10 μM fluo-4 AM (Invitrogen) and 0.1% Pluronic F-127 for 45 min at 37° C. Cardiac cell constructs (at least 9 samples from each group, from 3 separate experiments) were subsequently washed 3 times in modified Tyrode solution to allow de-esterification. Cell aggregates were electrically paced at 1-2 Hz using a bipolar platinum electrode placed in close contact with the cells using micromanipulator. The calcium transients were imaged using a confocal imaging system (LSM 510, Zeiss). The images were acquired with a EC Plan-Neofluar 10×/0.30M 27 objective lens at 216 frame/s 256×256 pixels and 2.5 um/pixel spatial resolution. Fluo 4 was excited at 488 nm diode laser. Fluorescence (F) was normalized by dividing by the basal cell fluorescence (F0) after dye loading.

Results

Figure 3:
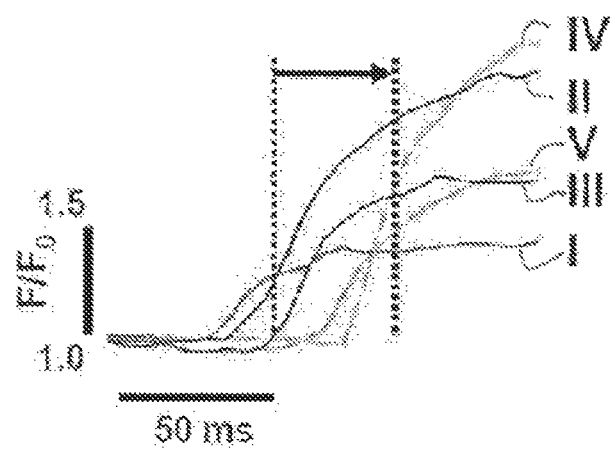
FIG. 3 is a graph of calcium transient propagation within the engineered tissues.

Calcium transients were only observed at the stimulation point in the unmodified scaffold. Calcium transients were observed at all points in the Alg-NW scaffold. See FIG. 3.

Calcium imaging within pristine scaffolds revealed activity only at the stimulation site, with negligible signal propagation to cells in adjacent pores. Analysis of the recording at six separate sites revealed calcium transients only at the stimulus point (I) but not at the nearest point, slightly more than 100 μm away. In contrast, the engineered tissue in the Alg-NW scaffolds contracted synchronously. In contrast to the lack of signal conduction in the absence of NWs, recordings at various sites revealed calcium transients throughout the scaffold, even though the stimulation point was remote. The calcium transients at sites I-V occurred in a temporal sequence determined by their spatial relationship to the source of stimulation, suggesting continuous propagation of a wavefront of cell depolarization.

Example 3

Analysis of Mechanical Properties within a 3D Alginate Scaffold with or without Gold Nanowires Seeded with Cardiac Cells Rheological testing of the alginate gel prior to lyophilization (which hardens it to its final firmness) showed that viscosity and elastic shear modulus increased with NW concentration, which suggests interactions between the polymer chains and/or the ionic cross-linker (in this case, calcium) and the NWs. The increased viscosity may also be caused by NWs acting as space fillers, increasing the strength of the hybrid material. These results are demonstrated by FIGS. 4A and 4B.

Figure 4A:
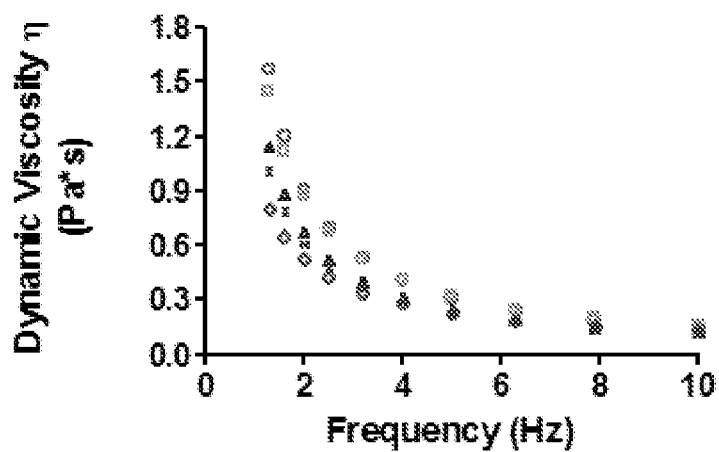
FIGS. 4A and 4B are graphs of the mechanical properties of the Alg-NR.
Figure 4B:
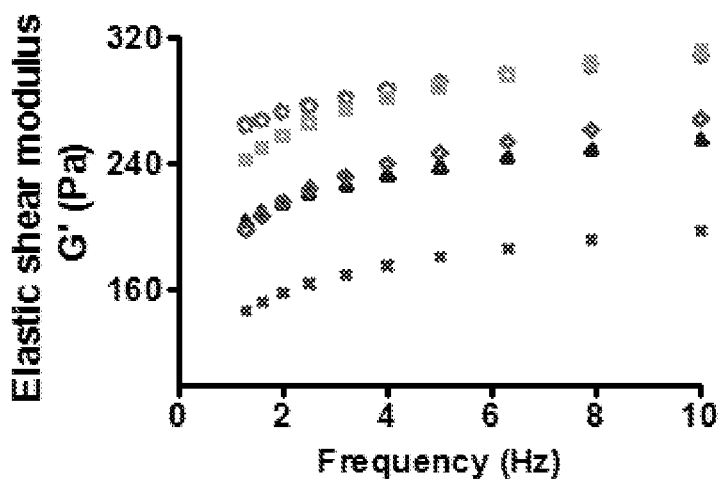

As shown by FIG. 4A, at higher concentrations of NWs the biomaterial became more viscous. As shown by FIG. 4B, increasing NW concentration increased the elastic shear modulus of the biomaterial. Elemental analysis of the features within the pore wall indicated they are made of gold.

Scanning electron microscopy (SEM) revealed NWs (0.5 mg/mL) either parallel to or penetrating the pore walls of the alginate scaffolds. At 1 mg/mL, the wires aggregated inside the scaffold pores, creating star-shaped structures with a length scale of 5 μm. Elemental analysis of these structures confirmed they were composed of gold. NW aggregates were homogeneously distributed throughout the scaffold, approximately 5-10 μm apart. The size scale and distribution of the NWs, and the fact that they were long enough to cross the pore walls, were important to increase the probability of interaction between cardiac cell bundles and of electrical signal transmission throughout the scaffold.

Example 4

Analysis of Topography and Conduction within a 3D Alginate Scaffold with or without Gold Nanowires Seeded with Cardiac Cells Materials and Methods Approximately 500 nm-thick films of Alg-NW were fabricated on indium tin oxide (ITO) conducting glass slides (backside contact) to simulate the Alg-NW scaffold pore wall and evaluate the bridging effect of NWs on the spatial conductivity of alginate surfaces. Conductive atomic force microscopy (C-AFM) was used to simultaneously measure the surface topography and conductance through the film Thin films were prepared by sandwiching alginate film (with or without NWs) between two ITO-coated slides (Sigma, 70-100 Ω/sq) Subsequent AFM measurements revealed that the resulting films were about 500 nm thick. For impedance measurements, an AC potential bias was applied between the ITO electrodes and swept the frequency between $10^6$ Hz and 1 Hz (0.1V amplitude, 0.022 decade/sec sweep rate). The real and imaginary components of the impedance at each frequency were recorded.

Conductivity and Topography Measurements by AFM

Topography and conductivity measurements were performed using an Asylum Research AFM (model MFP-3D) with Pt/Ir-coated probes (Veeco Instruments, SPM-PIC, 0.2 N/m spring constant, 13 kHz resonant frequency). For topography and current maps, the sample was rastered in contact mode with a 200 mV tip bias. Topography and current were recorded simultaneously. For current versus voltage curves, the tip was positioned either over a NW or alginate region. A triangular wave potential bias (4 cycles, 0.5 Hz, 1V amplitude) was applied to the tip, and the current was simultaneously recorded.

Results

Results are shown in FIGS. 2A-2E. The many coincident features in the topography and conductance plots indicated that nanowires fully bridged the film. At the NWs, current increased with bias voltage over the range −1 to 1V, while negligible current passed through NW-free regions of the alginate film over that same range. Alginate films containing gold nanorods, which are significantly shorter than the film thickness (average length approximately 60 nm and diameter of 30 nm), showed topographic features similar to those containing NWs, but negligible electrical current passed through those films.

Figure 2E:
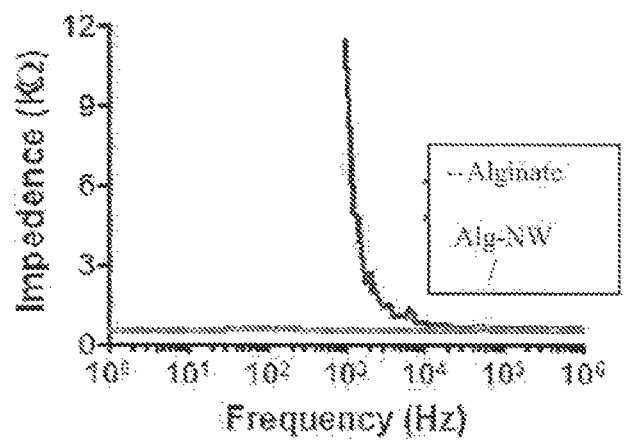

Further evidence of enhanced conductivity from incorporation of NWs was obtained by measuring the overall impedance of thin alginate films with or without Alg-NWs. Films were pressed between two ITO glass slides serving as electrodes and applying an AC bias with frequency swept between 1 MHz and 10 Hz (FIG. 2E). Both the composite and pure films exhibited low impedance at high frequencies, a result of the high capacitance of the film itself. At frequencies nearer DC, the impedance of the composite membrane was consistently lower than that of the pure film, a finding attributable to the low parallel resistance introduced by the bridging nanowires. Below $10^3$ Hz, the pure alginate film was not sufficiently conductive to yield reliable measurements.

Example 5

Analysis of Cell Viability within a 3D Alginate Scaffold with or without Gold Nanowires Seeded with Cardiac Cells Materials and Methods Cell viability within the scaffolds was assessed by a metabolic activity assay (XTT assay). Results are normalized to day 0 values. N=6 for each group at each time point.

The functional improvement of the engineered cardiac construct by incorporation of conducting nanowires was demonstrated electrophysiologically. Cardiac cell constructs with or without NWs were incubated with a calcium imaging dye, and calcium propagation was imaged by fluorescence microscopy. Isolated cardiac cell aggregates from each group were stimulated by applying a local electrical field using micro electrodes connected to a micromanipulator. The propagation and fluorescence intensity of the calcium dye in the engineered tissue were recorded videographically and plotted. Recordings were performed at room temperature to prevent spontaneous contraction and therefore calcium propagation in non-stimulated sites.

Results

Figure 5:
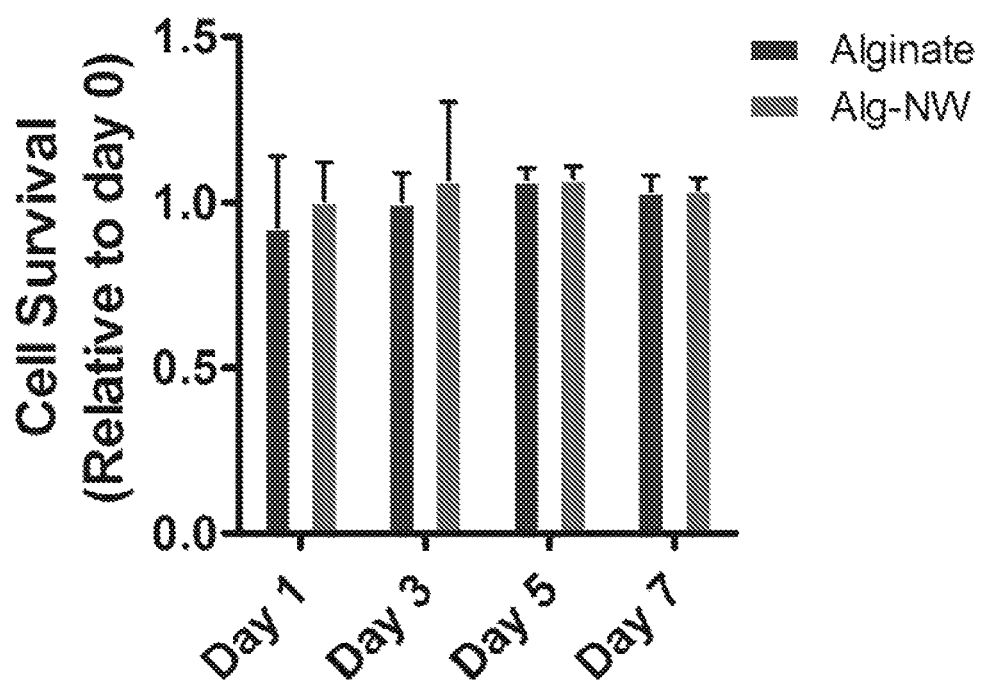
FIG. 5 is a graph of cell viability (relative to day zero) on days 1, 3, 5 and 7.

Results are shown in FIG. 5. As a preliminary to functional studies, the cytotoxicity of the NWs embedded within the scaffolds was evaluated by seeding them with cardiac cells isolated from the left ventricles of neonatal rats and following cell viability. Metabolic activity assay of the cardiac cell constructs suggested no cytotoxic effect due to NW incorporation.

These results demonstrate that inorganic nanostructures can be used to enhance the structure, phenotype, and function of engineered cardiac tissue.

Modifications and variations will be obvious to those skilled in the art and are intended to come within the scope of the appended claims.

We claim:

1. A three dimensional macroporous nanocomposite comprising electrically conductive nanowires having a diameter of 50 nm or less and a wire length longer than 500 nm embedded within a porous, polymeric non-conductive matrix which allows cellular ingrowth or seeding of cells, wherein the pore size is between 50 µm and 100 µm in diameter, and wherein the nanowires bridge the pore walls of the non-conductive matrix to enable electrical communication between cells on either side of the pore walls.

2. The nanocomposite of claim 1, wherein the nanowire is a metallic nanowire.

3. The nanocomposite of claim 2, wherein the metallic nanowire comprises one or more metals selected from the group consisting of nickel, platinum, gold, stainless steel, and combinations thereof.

4. The nanocomposite of claim 1, wherein the nanowire is a molecular nanowire.

5. The nanocomposite of claim 4, wherein the molecular nanowire is organic or inorganic.

6. The nanocomposite of claim 1, wherein the matrix is a natural polymer.

7. The nanocomposite of claim 1, wherein the matrix is a gel or forms a gel.

8. The nanocomposite of claim 1, wherein the matrix is about 90% porous.

9. The nanocomposite of claim 1 wherein the nanowires are parallel to and/or penetrate the pores of the biomaterial.

10. The nanocomposite of claim 1, wherein the nanowires are aggregated to form structures.

11. The nanocomposite of claim 1, wherein the nanowires are homogeneously distributed within the biomaterial.

12. The nanocomposite of claim 1, wherein the nanocomposite further comprises a therapeutic, diagnostic, and/or prophylactic agent.

13. A method of making a three dimensional macroporous nanocomposite having a pore size is between 50 µm and 100 µm in diameter and electrically conductive nanowires having a diameter of 50 nm or less and a wire length longer than 500 nm comprising
 (a) mixing electrically conductive nanowires having a diameter of 50 nm or less and a wire length longer than 500 nm with a polymeric matrix to embed the nanowires in the matrix;
 (b) freezing the nanowires and the matrix; and
 (c) lyophilizing the frozen nanowires and matrix.

14. The method of claim 13, wherein the polymeric matrix and the nanowires are cross-linked to form a gel prior to freezing.

15. The nanocomposite of claim 1 comprising electrically conductive nanowires having a diameter of 50 nm or less and a wire length longer than 500 nm embedded within and bridging pores of the polymeric matrix seeded with cardiomyocytes.

16. A method of treating myocardial infarction comprising the nanocomposite of claim 15 into or onto cardiac tissue of a patient in need thereof and passing an electrical stimulation of up to 5 Volts/cm, 1 Hz across the nanocomposite.

17. The method of claim 16 wherein the nanocomposite is seeded with cardiomyocytes or cells forming cardiomyocytes prior to implantation.

18. The method of claim 16 wherein the nanocomposite is applied to the heart at a site in need of repair or regeneration and the electrical stimulation is applied from an external source.

19. The nanocomposite of claim 1 wherein the nanowires are at a distance of about five microns from each other.

20. The nanocomposite of claim 1 wherein the nanowires are star-shaped.

* * * * *